United States Patent [19]

Xiaoming et al.

[11] Patent Number: 5,607,643
[45] Date of Patent: Mar. 4, 1997

[54] METHOD OF AND APPARATUS FOR ANALYZING IMMUITY BY RAMAN SPECTROMETRY

[75] Inventors: Dou Xiaoming; Toshio Takama, both of Kyoto, Japan

[73] Assignee: Kyoto Dai-ichi Kagaku Co., Ltd., Japan

[21] Appl. No.: 339,710

[22] Filed: Nov. 14, 1994

[30] Foreign Application Priority Data

Nov. 19, 1993 [JP] Japan .................. 5-314587

[51] Int. Cl.⁶ .................. G01N 21/03; G01N 21/01
[52] U.S. Cl. .................. 422/82.05; 422/52; 422/64; 422/65; 422/69; 356/244; 356/301
[58] Field of Search .................. 356/244, 301; 422/52, 64, 65, 69, 82.05, 54

[56] References Cited

U.S. PATENT DOCUMENTS

| | | |
|---|---|---|
| 3,797,940 | 3/1974 | King . |
| 4,053,229 | 10/1977 | McCluney .................. 356/103 |
| 4,213,703 | 7/1980 | Haunold et al. .................. 422/54 X |
| 4,505,586 | 3/1985 | Tochigi et al. .................. 356/301 |
| 5,037,200 | 8/1991 | Kodama .................. 356/301 X |
| 5,092,674 | 3/1992 | Garner .................. 356/244 |
| 5,119,789 | 6/1992 | Kajiwara et al. . |
| 5,241,363 | 8/1993 | Garner .................. 356/244 X |
| 5,347,358 | 9/1994 | Nebe et al. . |

FOREIGN PATENT DOCUMENTS

| | | |
|---|---|---|
| 4123178 | 1/1992 | Denmark . |
| 587008 | 3/1994 | European Pat. Off. . |
| 634642 | 1/1995 | European Pat. Off. . |
| 1583216 | 10/1969 | France . |
| 2693796 | 1/1994 | France . |

OTHER PUBLICATIONS

R. F. Stamm *Encycl. Ind. Chem. Anal.* 1966, 3, 305–333.
A. Timidei et al. *Chem. Instrum.* 1969, 2, 117–120.
J. Sturm et al. *Indian J. Pure Appl. Phys.* 1978, 16, 327–334.
E. G. Rodgers et al. *Appl. Spectrosc.* 1981, 35, 215–217.
K. Kneipp et al. *Stud. Phys. Theor. Chem.* 1987, 45, 451–457.
Y. Wang et al. *Anal. Chem.* 1989, 61, 2647–2651.
I. R. Nabiev et al, *J. Raman Spectrosc.* 1990, 21, 333–336.
N.-T. Yu et al. *J. Raman Spectrosc.* 1990, 21, 797–802.
K. Kneipp et al. *J. Molec. Struct.* 1991, 183–192.
B. N. Rospendowski et al. *J. Am. Chem. Soc.* 1991, 1217–1225.
R. L. Garrell *J. Bioact. Compat. Polym.* 1991, 6, 296–307.
J. J. Laserna et al. *Spectroscopy* 1991, 6, 34–38.
L. D. Barron et al. *Faraday Discuss.* 1992, 93, 259–268.
B. N. Rospedowski et al. *Eur. Biophys. J.* 1992, 21, 256–261.
J. J. Laserna et al. *Anal. Chem.* 1992, 64, 2006–2009.
C. Fagnano et al. *J. Raman Spectrosc.* 1992, 23, 637–639.
L. M. Cabalin et al. *Quim. Anal.* 1993, 12, 209–213.
K. Ito *Bunseki* 1993, (8), 577–585.
J. J. Laserna *Anal. Chim. Acta.* 1993, 283, 607–622.

(List continued on next page.)

*Primary Examiner*—Arlen Soderquist
*Attorney, Agent, or Firm*—Nikaido, Marmelstein, Murray & Oram, LLP

[57] ABSTRACT

A cell storing a sample prepared by adsorbing an immunocomplex which is formed by antigen-antibody reaction on a surface of a noble metal colloid such as a gold colloid as an immunity test material is irradiated with excitation light from a light source by an optical system. Raman scattering light generated from the sample is guided to and detected by a spectral detector through an optical system. A signal processing arithmetic unit corrects the Raman scattering light which is detected by the spectral detector with an output of the detector indicating intensity of the light source for obtaining a Raman spectrum, thereby identifying or determining a measuring object material.

3 Claims, 6 Drawing Sheets

OTHER PUBLICATIONS

S. Chadha et al. *Rev. Sci. Instrum.* 1993, 64, 3088–3093.

I. Nabiev et al. *J. Raman Spectrosc.* 1994, 25, 13–23.

Analytical Biochemistry, vol. 182, No. 2, Nov. 1, 1989 New York, US, pp. 388–398, T. E. Rohr et al 'Immunoassay employing surface–enhanced Raman spectroscopy' p. 388, right column, line 15—line 29, p. 397, right column, line 24—line 28.

Review of Scientific Instruments, vol. 54, No. 10 10 Oct. 1983 New York, US, pp. 1364–1367, M. Pezolet 'Thermo-electrically regulated sample holder for Raman spectroscopy' abstract, p. 1364, left column, paragraph 1, p. 1364 left column, paragraph 4, p. 1365, left column, line 1, figures 1 and 2.

METHOD OF AND APPARATUS FOR ANALYZING IMMUITY BY RAMAN SPECTROMETRY

BACKGROUND OF THE INVENTION

1. Field of the Invention

The present invention relates to a method of and an apparatus for immunologically analyzing a measuring object in the field of clinical testing, biochemical sample measurement, drug quality control or the like.

2. Description of the Background Art

Immunological analysis methods employing antigen-antibody reaction include fluorescent immunoassay and luminescent immunoassay. These methods are adapted to competitively react an antigen, which is labeled with a fluorescent material or a chemiluminescent material, with a measuring object antigen with respect to an antibody for measuring fluorescence or luminescence from the label of an antigen-antibody reacted immunocomplex, thereby quantitatively analyzing the measuring object material.

A method of adding an antigen or an antibody of a measuring object material to an antibody or an antigen and measuring light absorption or scattering by an immunocomplex which is formed by antigen-antibody reaction thereby making quantitative analysis is known as an optical measuring method utilizing neither fluorescence nor luminescence. Quantitative analysis methods employing light scattering include turbidimetry and nephelometry, which are adapted to measure transmitted light attenuated by absorption and scattering and to measure intensity of scattered light respectively.

The method employing light scattering measures Rayleigh or Mie scattering, in response to sizes of particles as measured. No wavelength shifting is caused in Rayleigh or Mie scattering, and scattering intensity at an excitation light wavelength is measured.

On the other hand, surface-sensitized Raman spectrometry is employed as a method of measuring vibration spectra of molecules. This method utilizes such a phenomenon that strong Raman scattering is caused when a material is adsorbed on the surface of a noble metal electrode or colloid of gold or silver (refer to "Bunseki", 1993, pp. 577–585, for example). Protein, bilirubin and the like are studied through such surface-sensitized Raman spectrometry. It is known that vibration spectra are enhanced to $10^7$ to $10^8$ times upon occurrence of surface-sensitized Raman scattering, to allow measurement of high sensitivity.

However, fluorescent or luminescent immunoassay requires complicated chemical treatment for labelling an antigen or an antibody with a fluorescent or chemiluminescent material. In general, further, such immunoassay is heterogeneous immunoassay, which requires a B-F separating operation for separating an antigen-antibody reacted immunocomplex (B) from a nonreacted antigen (F) and a washing operation, leading to increase in number of analysis steps.

On the other hand, the method utilizing light scattering, which is homogeneous immunoassay, can be simply carried out with requirement for neither B-F separation nor washing. However, the method employing Rayleigh or Mie scattering has a problem of low detection sensitivity and low measurement accuracy as to a low concentration material.

Although study of the surface-sensitized Raman spectrometry is made on protein and bilirubin, there has been made no report on measurement of surface-sensitized Raman scattering in relation to an immunocomplex which is formed through antigen-antibody reaction.

SUMMARY OF THE INVENTION

A first object of the present invention is to provide an immunity analyzing method which can measure immunity in high sensitivity with no requirement for complicated chemical treatment for labeling.

A second object of the present invention is to provide a method which can implement homogeneous immunoassay.

A third object of the present invention is to provide a measuring apparatus comprising a cell, which can stably carry out the aforementioned immunity analyzing method.

According to study made by the inventors, a Raman signal which is obtained in a state of adsorbing an antibody or an antigen on a surface of a noble metal colloid can be distinguished from a Raman scattering signal which is obtained in a state of adding an antigen or an antibody thereto for causing antigen-antibody reaction and adsorbing an immunocomplex on the colloid surface. The present invention has been proposed on the basis of this recognition, and is adapted to enable at least either qualitative or quantitative analysis of an antigen or an antibody by measurement of Raman scattering.

A method of analyzing immunity according to the present invention is adapted to adsorb an immunity test material of an antigen-antibody reacted immunocomplex on surfaces of particles forming a noble metal colloid and irradiate the colloid with monochromatic excitation light, for spectroscopically analyzing Raman scattering light as generated.

The present invention will not reject application to inhomogeneous immunoassay, while an antibody or an antigen is previously adsorbed on surfaces of particles forming a noble metal colloid, an antigen or an antibody of a measuring object which is antigen-antibody reacted with the antibody or the antigen is added to cause antigen-antibody reaction, and thereafter the colloid is irradiated with excitation light with no B-F separation to carry out homogeneous immunoassay in a preferred mode of the present invention.

An apparatus according to the present invention comprises a cell storing a sample which is prepared by adsorbing an immunity test material on surfaces of particles forming a noble metal colloid, a light source part for irradiating the sample which is stored in the cell with excitation light, and a spectral detection part for spectrally detecting Raman scattering light from the sample which is stored in the cell, while the cell includes an electronic cooling/heating element, a temperature sensor and a temperature controller for controlling energization of the electronic cooling/heating element by an output of the temperature sensor thereby maintaining the cell at a constant temperature.

A colloid of gold, silver or copper can be employed as the noble metal colloid. A proper particle diameter for the colloid is 5 to 50 nm.

An antigen of a measuring object material is added to a noble metal colloid which is prepared by previously adsorbing an antibody on surfaces of its particles to cause antigen-antibody reaction, so that an immunocomplex which is formed by the antigen-antibody reaction is adsorbed on the colloid surface. In this state, the colloid is irradiated with excitation light, to cause surface sensitized Raman scattering. The wavelength of Raman scattering light is shifted with respect to that of the excitation light by a frequency caused by internal vibration of the immunocomplex material which is adsorbed on the colloid surface. It is possible to identify the immunocomplex as formed from a Raman spectrum by spectroscopically detecting the Raman scattering light, while determining the object material as added from the intensity of the Raman scattering light.

When a sample is irradiated with excitation light, the sample temperature is increased. Since surface sensitized Raman scattering is influenced by the temperature, it is possible to avoid increase of the sample temperature caused by irradiation with the excitation light, by maintaining the cell at a constant temperature by the inventive device.

The present invention is adapted to analyze immunity on the basis of the fact that surface sensitized Raman scattering is caused when an immunocomplex is adsorbed on surfaces of particles forming a noble metal colloid, and analysis can be made in high sensitivity since Raman scattering is enhanced to $10^7$ to $10^8$ times upon sensitization.

According to the present invention, the operation is simplified since it is possible to implement homogeneous immunoassay requiring neither B-F separation nor a washing operation.

It is possible to enable analysis of a small amount of sample while avoiding influence caused by temperature change of the sample, by maintaining the cell for measuring the sample at a constant temperature by the electronic cooling/heating element.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
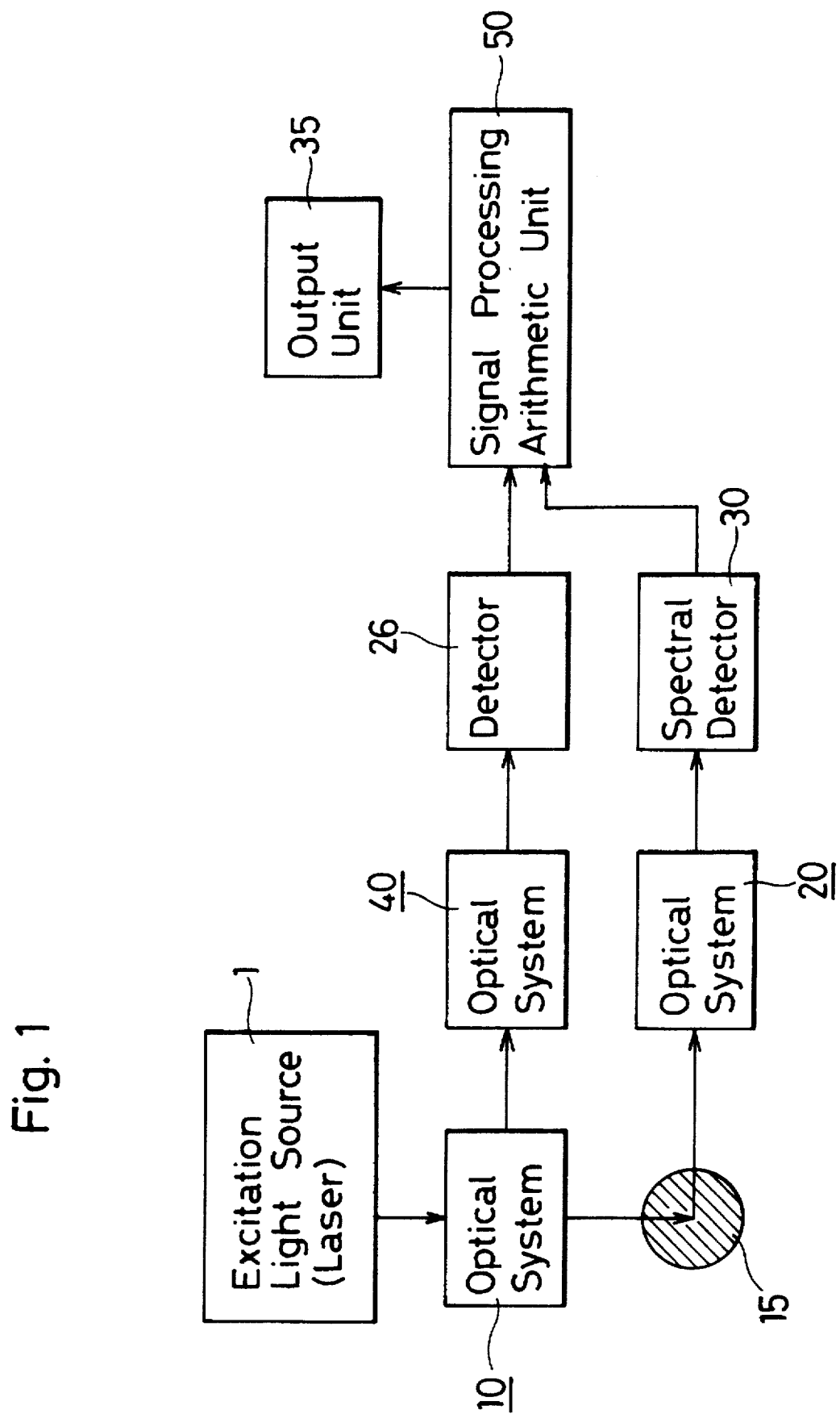
FIG. 1 is a block diagram schematically showing optical systems for carrying out the present invention.

FIG. 1 shows an immunity analyzer according to an embodiment of the present invention.

A cell 15 stores a colloid sample prepared by adsorbing an immunocomplex which is formed by antigen-antibody reaction on a surface of a noble metal colloid such as a gold colloid as an immunity test material. Numeral 1 denotes an excitation light source, which is formed by a laser unit, for measuring Raman scattering light. The laser unit can be selected from lasers having wide ranges of wavelengths over near-ultraviolet to near-infrared regions such as a continuously oscillating Ar ion laser, a Kr ion laser, an He-Ne laser and an He-Cd laser, and a pulse laser such as an Nd:YAG laser. When spontaneous emission light of the laser unit is screened so that only an oscillation beam is utilized as the excitation light, the laser unit may be combined with an interference filter or a spectroscope. Alternatively, the spontaneous emission light may also be simultaneously applied to carry out wavelength calibration of a spectrum.

The excitation light generated from the light source 1 is separated by an optical system 10 into a measuring beam and a reference beam, so that the measuring beam is adjusted by the optical system 10 and applied to the sample which is stored in the cell 15. Raman scattering light generated from the sample is taken out in a direction which is at an angle of 90° with respect to the direction of incidence of the measuring beam, and detected by a spectral detector 30 including a spectroscope through an optical system 20 for adjusting the luminous flux.

On the other hand, the reference beam is detected by a detector 26 through an optical system 40 for luminous flux adjustment, in order to correct fluctuation of excitation light intensity. A signal processing arithmetic unit 50 corrects the Raman scattering light which is detected by the spectral detector 30 with an output of the detector 26 indicating light source intensity to obtain a Raman spectrum, thereby identifying or determining the measuring object material. Numeral 35 denotes an output unit such as a printer or a CRT.

Figure 2:
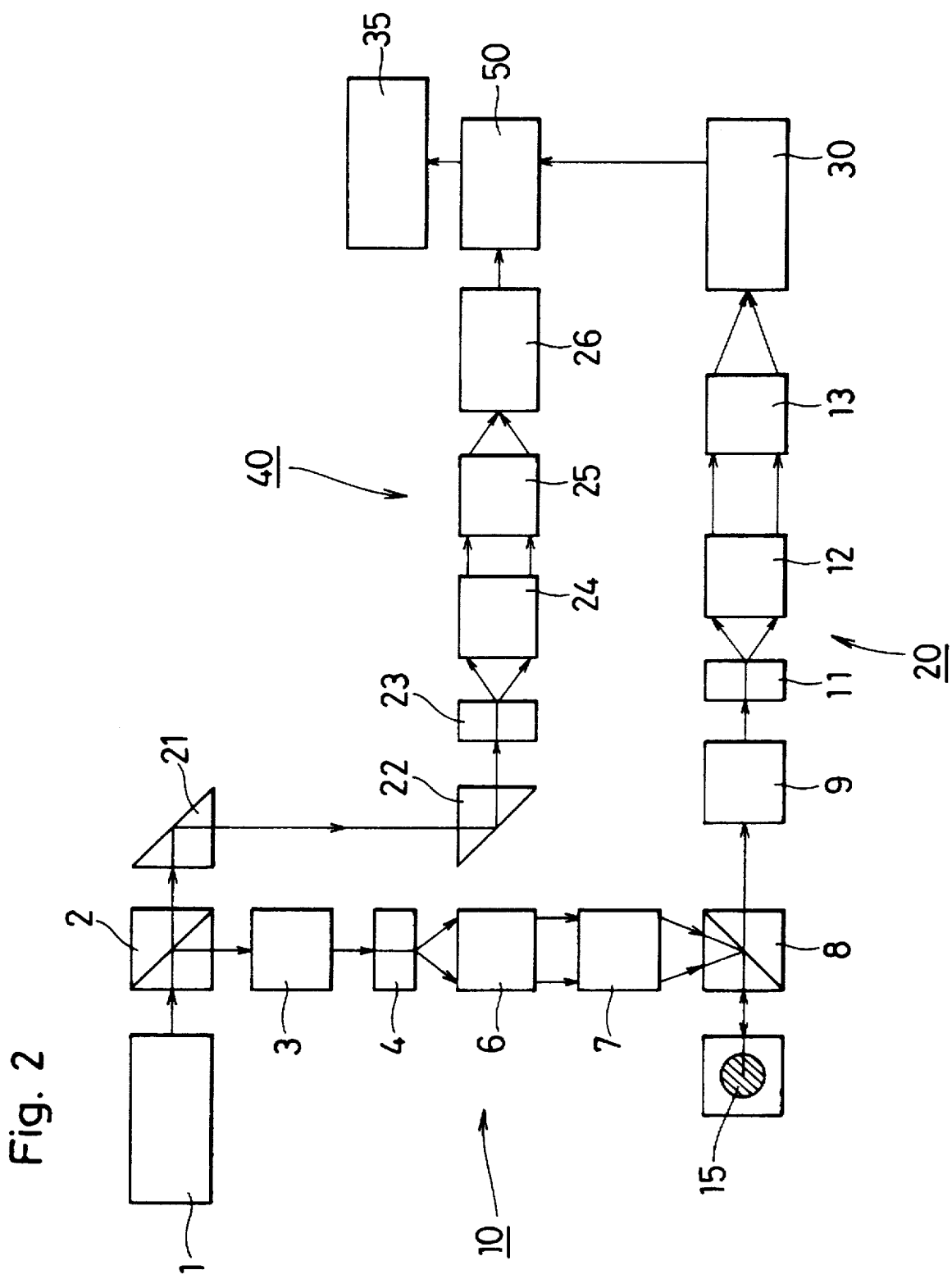
FIG. 2 is a block diagram showing optical systems according to an embodiment of the present invention in detail.

FIG. 2 shows the optical systems in detail. A beam splitter 2 for separating the luminous flux of the excitation light which is received from the laser light source 1 into the measuring beam and the reference beam, a convex lens 3 for condensing the measuring beam which is separated by the beam splitter 2, convex lenses 6 and 7 for adjusting the luminous flux, and a beam splitter 8 for reflecting the measuring beam and guiding the same to the sample which is stored in the cell 15 are arranged along the optical path of the measuring beam, as the optical system 10 for irradiating the sample with the luminous flux serving as the measuring beam. On the optical path of the measuring beam, further, a filter 4 is provided between the convex lenses 3 and 6 for selecting a laser beam of one wavelength from a plurality 1. of oscillation beams received from the laser light source On the other hand, a convex lens 9 for condensing the Raman scattering light and the measuring beam transmitted through the beam splitter 8 and convex lenses 12 and 13 for adjusting the luminous flux are arranged along the optical path of the Raman scattering beam which is generated from the sample stored in the cell 15, as the optical system 20 for extracting the Raman scattering light in a direction which is at an angle of 180° with respect to the direction of incidence of the measuring beam. A filter 11 for removing an excitation light component is provided between the convex lenses 9 and 12.

On a reference beam side, further, reflecting mirrors 21 and 22 for bending the optical path and convex lenses 24 and 25 for adjusting the luminous flux are arranged along the optical path, in order to guide the contrast beam to the detector 26. A filter 23 of the same wavelength characteristics as the filter 4 provided on the measuring beam side is provided between the reflecting mirror 2 and the convex lens 24.

Figure 3:
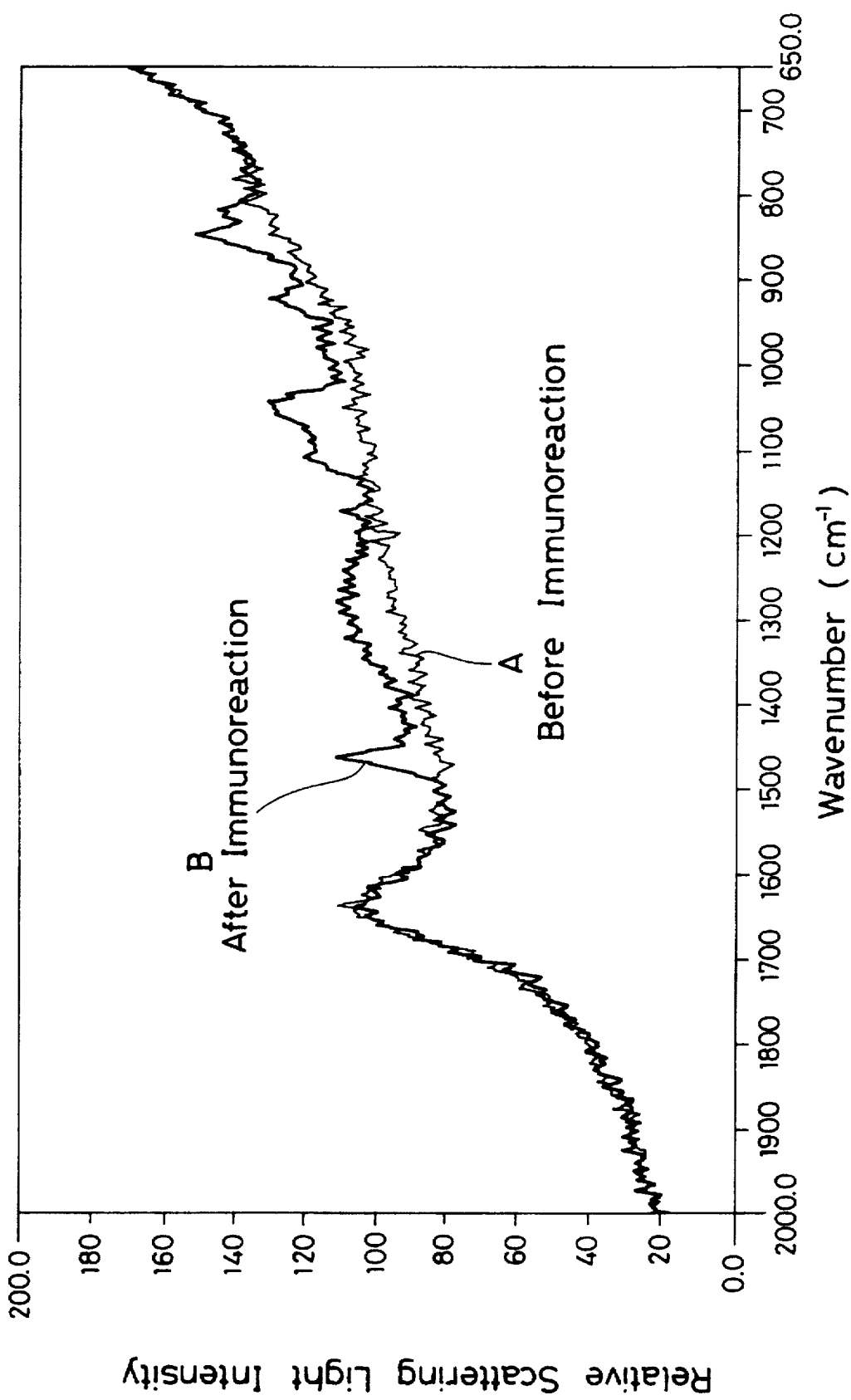
FIG. 3 is a waveform diagram showing Raman spectra before and after immunity reaction in the embodiment of the present invention.

FIG. 3 shows a Raman spectrum (before immunoreaction) A obtained from an IgG antibody which was adsorbed on surfaces of gold colloid particles and a Raman spectrum (after immunoreaction) B obtained after adding an antigen IgG to the sample in contrast, as exemplary Raman spectra. The ordinate shows relative scattering light intensity relatively indicating amounts of received light with reference to a level 0 with no light received on the measuring device, and the abscissa shows wavenumbers.

The gold colloid adsorbing the IgG antibody on particle surfaces which was employed for carrying out this measurement was prepared by diluting ANTI-MOUSE IgG(H) (Goat) GOLD CONJUGATE, EM (product by BioCell, USA) having a particle diameter of 30 nm and concentration of 15 μg/ml to 100 times with 0.01M PBS (pH 7.4) containing 1% of BSA. Referring to FIG. 3, symbol A indicates the Raman spectrum obtained from the gold colloid adsorbing the antibody itself. On the other hand, symbol B indicates the Raman spectrum obtained after adding the sample to the gold colloid adsorbing the antibody to contain 0.1 ng/ml of a mouse IgG and causing antigen-antibody reaction. The light source 1 was prepared from a YAG laser, with an output of 300 mW.

Comparing the spectra A and B before and after immunoreaction shown in FIG. 3 with each other, characteristic bands appear in the vicinity of 1460 $cm^{-1}$, 1058 $cm^{-1}$, 835 $cm^{-1}$ etc. in the spectrum B after immunoreaction. This characteristic Raman scattering was caused by an immunocomplex which was formed by the antigen-antibody reaction caused on the gold colloid surface.

The spectrum B shown in FIG. 3 was obtained by making measurement without separating (BF separating) an unreacted free antigen after the antigen-antibody reaction. Namely, a characteristic Raman spectrum can be obtained without carrying out BF separation, whereby homogeneous immunoassay can be constructed.

An immunocomplex which is formed by antigen-antibody reaction is generally influenced by excitation light such that the same is decomposed or evaporated by temperature change caused by heat absorbed in a sample upon irradiation with a laser beam, or altered by light. In particular, a problem is caused in measurement of a colored sample or a high heat absorbing sample. Therefore, it is preferable to stably maintain a sample at a constant temperature by carrying out temperature control, in order to measure Raman scattering over a long time.

In general, measurement is made while fluctuating a sample, cooled air is blown to a sample for scattering heat, a sample is placed in a nitrogen gas jet, or a rotary cell is rotated at a high speed for making measurement while moving the same similarly to a centrifuge, as a method of maintaining the sample at a stable temperature. Thus, it is conceivable to apply such a method to the inventive Raman spectral measurement.

However, it is difficult to apply any of these methods to the present invention. For example, a considerable sample quantity is required for measuring a sample while fluctuating the same, and this method cannot be employed for measurement of a small amount of sample. In the method of placing the sample in cold air or a nitrogen gas jet, a cold gas generator is required and hence the analyzer is increased in size, leading to an inconvenient operation and difficulty in application. The rotary cell has been devised in expectation of preventing influence by high heat over a long time by moving the sample at a sufficiently high speed, while floating substances may adhere to an outer wall of the cell or samples are hardly mixed with each other by action of specific gravity separation caused by high-speed rotation since the cell which is rotated at a high speed acts similarly to a centrifuge. Further, the rotary cell also requires a sample quantity in excess of a certain degree.

Figure 4:
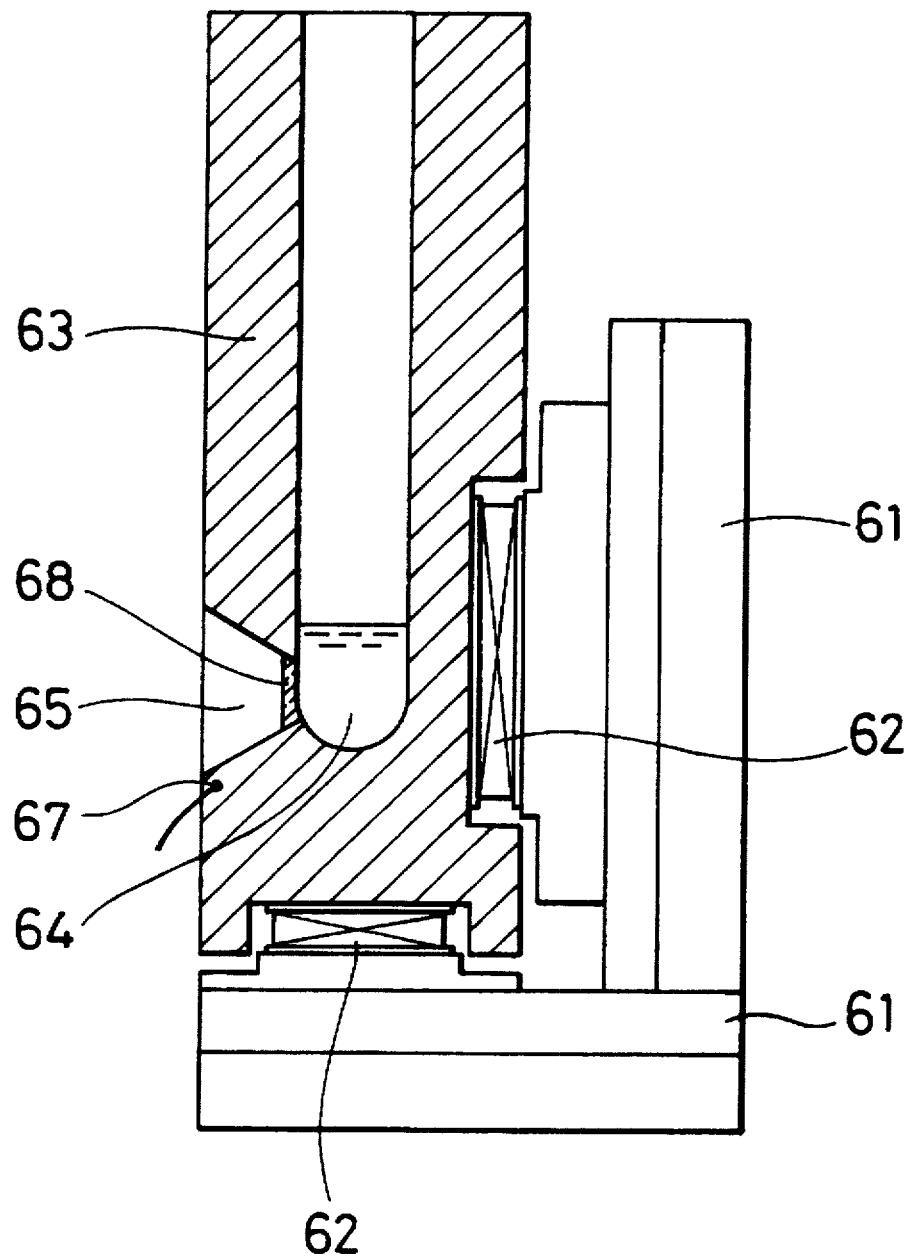
FIG. 4 is a vertical sectional view showing an example of a preferable cell.

FIG. 4 shows an exemplary cell for solving these problems.

Referring to FIG. 4, numeral 63 denotes an aluminum cell, comprising an aluminum metal block having a hole which is provided in its upper end toward its interior, for storing a sample. An inner surface of this hole is mirror-polished, and subjected to gold plating to be increased in infrared reflectance. A window 65 is provided in a bottom portion of the hole for applying excitation light to a sample 64 from the exterior and taking out Raman scattering light from the sample 64 toward the exterior, while a quartz glass window plate 68 is fitted in this window 65. In the metal block forming the cell 63, Peltier elements 62, 62 serving as electronic cooling/heating elements are provided on side and bottom portions of the hole respectively. The cell 63 is in contact with heat absorption sides of the Peltier elements 62, 62, while diffusion plates 61 are in contact with heat radiation sides of the Peltier elements 62, 62. A temperature sensor 67 is embedded in the metal block forming the cell 63. In the cell 63 shown in FIG. 4, the direction of incidence of excitation light is at 180° with respect to the direction for taking out the Raman scattering light.

Figure 5:
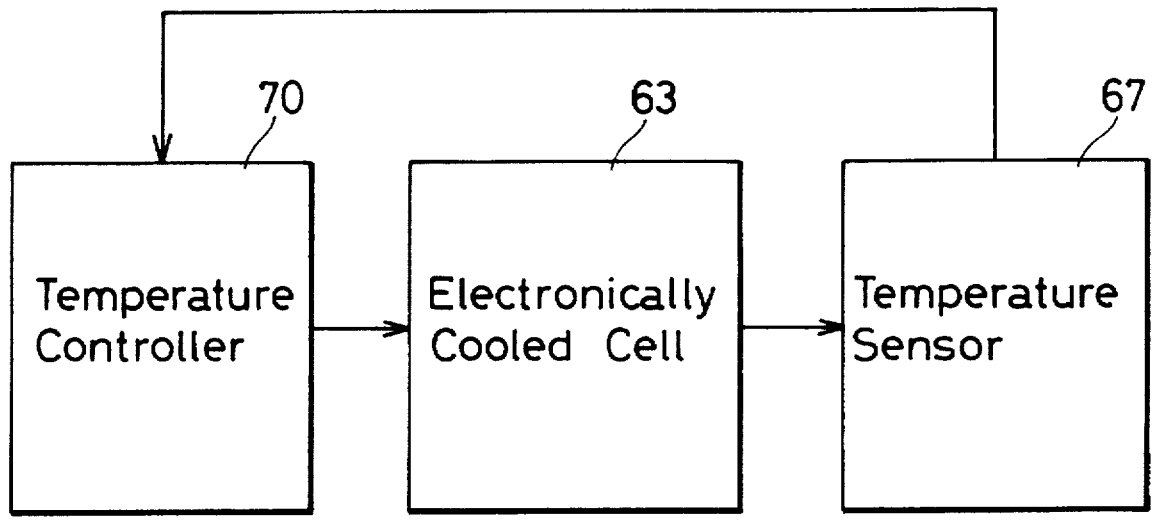
FIG. 5 is a block diagram showing a temperature control system for the cell shown in FIG. 4.

In order to maintain this cell 63 at a constant temperature, a temperature controller 70 is provided as shown in FIG. 5, for incorporating a detection signal of the temperature sensor 67 and controlling the amounts of currents to be fed to the Peltier elements 62, 62. When the temperature of the sample 64 irradiated with the excitation light is increased, the temperature controller 70 controls the amounts of energization to the Peltier elements 62, 62 for reducing the temperature of the cell 63 to an initial set temperature.

Figure 6:
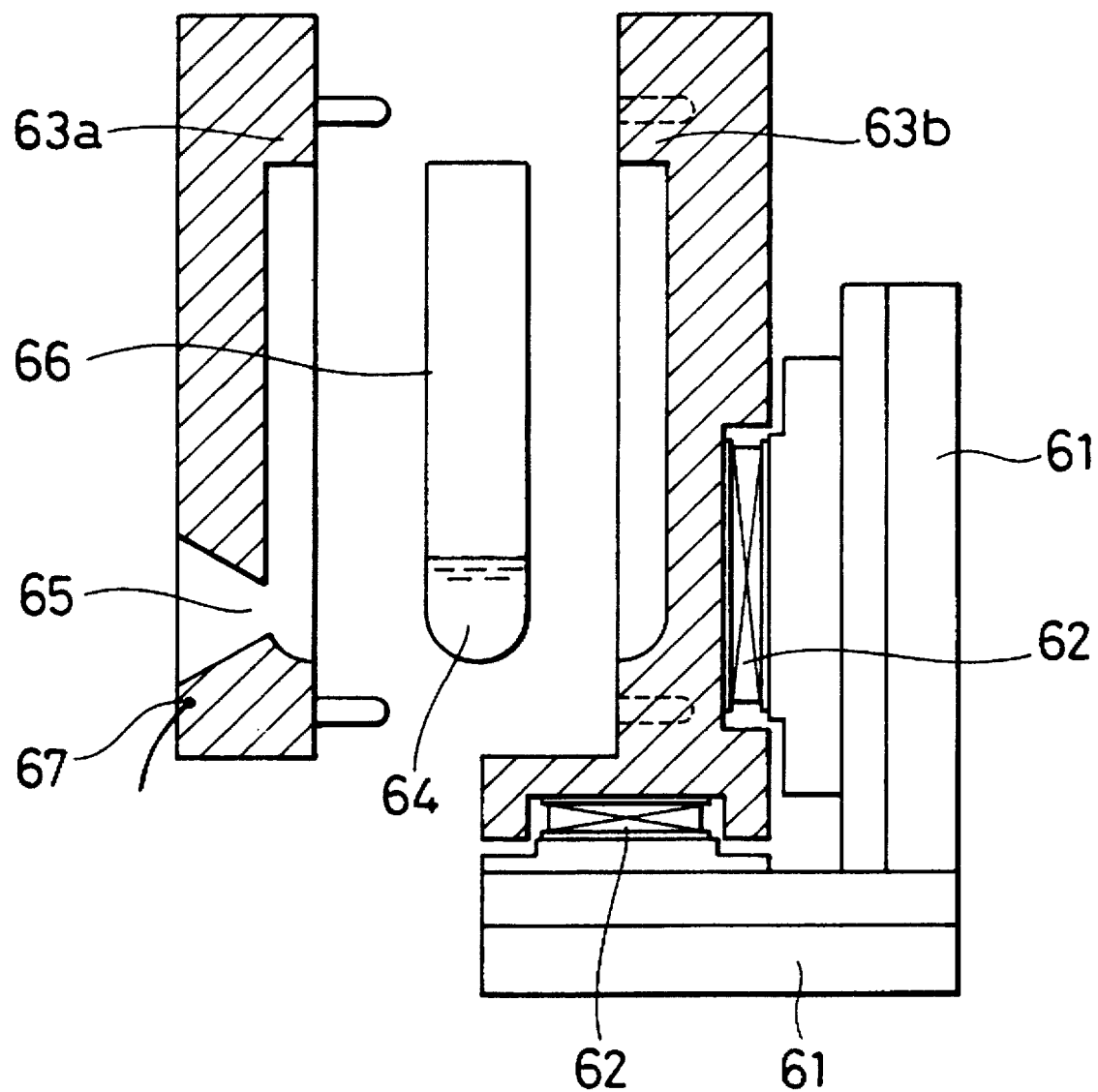
FIG. 6 is a partially fragmented vertical sectional view showing another example of a preferable cell.

FIG. 6 shows another exemplary cell. As compared with the cell 63 shown in FIG. 4 which is integrally formed by hollowing the metal block, a quartz glass cell 66 is employed in FIG. 6. An aluminum metal block is divided into two portions 63a and 63b, while cavities for storing the cell 66 are formed in opposite parts of these portions 63a and 63b, so that the portions 63a and 63b of the metal block are combined with each other to enclose the cell 66 with the cavities. The cell 66 is in contact with the metal block formed by the portions 63a and 63b which are combined with each other. A window 65 is formed in a position of the metal block portion 63a corresponding to a bottom portion of the cell 66, in order to apply excitation light and to take out Raman scattering light. Peltier elements 62, 62 for controlling the temperature are so mounted that heat absorption sides thereof are in contact with the metal block portion 63b, while diffusion plates 61 are provided on heat radiation sides of the Peltier elements 62, 62 and a temperature sensor 67 is embedded in the metal block portion 63a.

When the cell shown in FIG. 4 or 6 is employed, it is possible to prevent the influence by temperature change such that the sample is decomposed or evaporated by light or heat of excitation light for Raman spectral measurement or the spectrum is instabilized. This cell also enables analysis of a fine amount of sample.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An immunity analyzer comprising:

a sample cell storing a sample being prepared by adsorbing an immunity test material on surfaces of particles forming a noble metal colloid;

a light source part for irradiating said sample being stored in said sample cell with excitation light; and a spectral detection part of spectroscopically detecting Raman scattering light from said sample being stored in said sample cell, said sample cell providing an electronic cooling/heating element, a temperature sensor, and a temperature controller for controlling energization of said electronic cooling/heating element by an output of said temperature sensor thereby maintaining said cell at a constant temperature wherein said sample cell is formed by a heat conductive metal block having a hole provided in its upper end toward its interior for storing said sample, said hole being provided with a mirror-polished inner surface being subjected to gold plating, and a bottom portion having a window for receiving said excitation light and emitting said Raman scattering light with a quartz glass window plate being fitted, therein.

2. An immunity analyzer comprising:

a sample cell storing a sample being prepared by adsorbing an immunity test material on surfaces of particles forming a noble metal colloid;

a light source part for irradiating said sample being stored in said sample cell with excitation light; and a spectral detection part of spectroscopically detecting Raman scattering light from said sample being stored in said sample cell, said sample cell providing an electronic cooling/heating element, a temperature sensor, and a temperature controller for controlling energization of said electronic cooling/heating element by an output of said temperature sensor thereby maintaining said cell at a constant temperature wherein said sample cell comprises:
 a quartz glass cell, and
 a heat conductive metal block having a hole in its upper end toward its interior for storing said quartz glass cell, said hole being provided in its bottom portion with a window for receiving said excitation light and emitting said Raman scattering light,
 said electronic cooling/heating element and said temperature sensor being provided on said metal block.

3. An immunity analyzer in accordance with claim 2, wherein said metal block comprises two portions being combined with each other for defining said hole for storing said quartz glass cell.

* * * * *

UNITED STATES PATENT AND TRADEMARK OFFICE
CERTIFICATE OF CORRECTION

PATENT NO.    : 5,607,643
DATED         : March 4, 1997
INVENTOR(S)   : Xiaoming et al.

It is certified that error appears in the above-indentified patent and that said Letters Patent is hereby corrected as shown below:

Title page, item [54], col. 1, line 2, delete "IMMUITY" insert --IMMUNITY --.

Signed and Sealed this

Twentieth Day of May, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,607,643
DATED : March 4, 1997
INVENTOR(S) : DOU et al.

It is certified that error appears in the above-indentified patent and that said Letters Patent is hereby corrected as shown below:

```
    Title page,
Item [75], line 1 please delete "Dou Xiaoming" insert therefor --Xiaoming Dou--.
```

Signed and Sealed this

Thirteenth Day of January, 1998

Attest:

BRUCE LEHMAN

*Attesting Officer*    *Commissioner of Patents and Trademarks*